(12) United States Patent
Murakami et al.

(10) Patent No.: US 9,808,530 B2
(45) Date of Patent: Nov. 7, 2017

(54) COMPOSITION OF TIACUMICIN COMPOUNDS

(71) Applicant: Astellas Pharma Europe Ltd., Chertsey, Surrey (GB)

(72) Inventors: Yoshiyuki Murakami, Tokyo (JP); Hikaru Saito, Tokyo (JP)

(73) Assignee: Astellas Pharma Europe Ltd., Chertsey, Surrey (GB)

( * ) Notice: Subject to any disclaimer, the term of this patent is extended or adjusted under 35 U.S.C. 154(b) by 134 days.

(21) Appl. No.: 14/766,904

(22) PCT Filed: Jan. 14, 2014

(86) PCT No.: PCT/EP2014/000091
§ 371 (c)(1),
(2) Date: Aug. 10, 2015

(87) PCT Pub. No.: WO2014/111254
PCT Pub. Date: Jul. 24, 2014

(65) Prior Publication Data
US 2016/0045603 A1 Feb. 18, 2016

(30) Foreign Application Priority Data
Jan. 15, 2013 (EP) .................................. 13075002

(51) Int. Cl.
| | | |
|---|---|---|
| A61K 9/16 | (2006.01) | |
| A61K 31/7034 | (2006.01) | |
| A61K 31/7048 | (2006.01) | |
| A61K 47/36 | (2006.01) | |
| A61K 47/38 | (2006.01) | |
| A61K 9/00 | (2006.01) | |
| A61K 47/26 | (2006.01) | |

(52) U.S. Cl.
CPC ............ *A61K 47/38* (2013.01); *A61K 9/0095* (2013.01); *A61K 9/1652* (2013.01); *A61K 31/7034* (2013.01); *A61K 31/7048* (2013.01); *A61K 47/26* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 3,000,792 | A | 9/1961 | Denkewalter et al. |
| 3,978,211 | A | 8/1976 | Coronelli et al. |
| 4,632,902 | A | 12/1986 | Waters et al. |
| 4,918,174 | A | 4/1990 | McAlpine et al. |
| 5,583,115 | A | 12/1996 | McAlpine et al. |
| 5,653,940 | A | 8/1997 | Carey et al. |
| 5,767,096 | A | 6/1998 | Hochlowski et al. |
| 7,067,544 | B2 | 6/2006 | Hoefle et al. |
| 7,378,508 | B2 | 5/2008 | Chiu et al. |
| 7,507,564 | B2 | 3/2009 | Shue et al. |
| 7,863,249 | B2 | 1/2011 | Chiu et al. |
| 7,906,489 | B2 | 3/2011 | Shue et al. |
| 8,044,030 | B2 | 10/2011 | Ichikawa et al. |
| 8,445,654 | B2 | 5/2013 | Ichikawa et al. |
| 8,518,899 | B2 | 8/2013 | Chiu et al. |
| 8,586,551 | B2 | 11/2013 | Shue et al. |
| 8,728,796 | B2 | 5/2014 | Shue et al. |
| 8,859,510 | B2 | 10/2014 | Chiu et al. |
| 8,883,986 | B2 | 11/2014 | Chiu et al. |
| 8,916,527 | B2 | 12/2014 | Ichikawa et al. |
| 2003/0099699 | A1 | 5/2003 | Hanshew et al. |
| 2004/0224020 | A1 | 11/2004 | Schoenhard |
| 2006/0257981 | A1 | 11/2006 | Shue et al. |
| 2006/0269485 | A1 | 11/2006 | Friedman et al. |
| 2007/0105791 | A1 | 5/2007 | Sears et al. |
| 2007/0173462 | A1 | 7/2007 | Shue et al. |
| 2007/0259949 | A1 | 11/2007 | Chiu et al. |

(Continued)

FOREIGN PATENT DOCUMENTS

| | | |
|---|---|---|
| EP | 1326609 B1 | 8/2005 |
| JP | 2000-53514 A | 2/2000 |

(Continued)

OTHER PUBLICATIONS

Sullivan et al., "Fidaxomicin: A Macrocyclic Antibiotic for the Management of Clostridium difficile Infection," The Annals of Pharmacotherapy, vol. 44, pp. 352-359 (2010).
Swanson et al., "In vitro and in vivo evaluation of tiacumicins B and C against Clostridium difficile," Antimicrobial Agents and Chemotherpy, 35(6): 1108-1111 (1991).
Theriault et al., "Tiacumicins, a novel complex of 18-membered macrolide antibiotics. I. Taxonomy, fermentation and antibacterial activity," The Journal of Antibiotics, 40(5): 567-574 (1987).
The Condensed Chemical Dictionary, 10th Edition, Revised by Gessner G. Hawley, Published by Van Nostrand Reinhold Company pp. 34 and 835 (1981).
Vippagunta et al, "Crystalline solids," Advanced Drug Delivery Reviews, vol. 48. pp. 3-26 (2001).
Waterman, "Stabilization of Pharmaceuticals to Oxidative Degradation," Pharmaceutical Development and Technology, 7(1): 1-32 (2001).

(Continued)

*Primary Examiner* — Shaojia Anna Jiang
*Assistant Examiner* — Bahar Craigo
(74) *Attorney, Agent, or Firm* — Morgan, Lewis & Bockius LLP

(57) ABSTRACT

A composition comprising as the active ingredient one or more of a tiacumicin compound, a stereo-isomer thereof, a polymorph thereof or a solvate thereof, in combination with an excipient, selected from the group consisting of a xanthan gum, carrageenan, sodium alginate, guar gum, water dispersible cellulose (microcrystalline cellulose and sodium carboxymethylcellulose) and mixtures thereof is provided. Further, use of an excipient, selected from the group consisting of a xanthan gum, carrageenan, sodium alginate, guar gum, water dispersible cellulose (microcrystalline cellulose and sodium carboxymethylcellulose) and mixtures thereof as an anti-foaming agent in a composition comprising as the active ingredient one or more of a tiacumicin compound, a stereo-isomer thereof, a polymorph thereof or a solvate thereof is provided.

10 Claims, 12 Drawing Sheets

(56) References Cited

U.S. PATENT DOCUMENTS

| | | | |
|---|---|---|---|
| 2008/0193548 A1 | 8/2008 | Zanichelli et al. | |
| 2008/0194497 A1 | 8/2008 | Chiu et al. | |
| 2008/0206161 A1* | 8/2008 | Tamarkin | A61K 9/0014 424/45 |
| 2008/0269145 A1 | 10/2008 | Shue et al. | |
| 2009/0163428 A1 | 6/2009 | Chiu et al. | |
| 2010/0009925 A1 | 1/2010 | Shue et al. | |
| 2010/0010076 A1 | 1/2010 | Chiu et al. | |
| 2010/0035833 A1 | 2/2010 | Ichikawa | |
| 2010/0081800 A1 | 4/2010 | Chiu et al. | |
| 2013/0065844 A1 | 3/2013 | Sanghvi et al. | |
| 2013/0123477 A1 | 5/2013 | Shue et al. | |
| 2013/0252912 A1 | 9/2013 | Ichikawa et al. | |
| 2013/0252913 A1 | 9/2013 | Shue et al. | |
| 2013/0274175 A1 | 10/2013 | Shue et al. | |
| 2014/0107054 A1 | 4/2014 | Sears et al. | |

FOREIGN PATENT DOCUMENTS

| | | |
|---|---|---|
| JP | 2000-72760 A | 3/2000 |
| JP | 2000-239266 A | 9/2000 |
| WO | 98/02447 | 1/1988 |
| WO | 96/35702 | 11/1996 |
| WO | 2004/014295 A2 | 2/2004 |
| WO | 2005/112990 A2 | 12/2005 |
| WO | 2006/085838 A1 | 8/2006 |
| WO | 2007/048059 A2 | 4/2007 |
| WO | 2008/091518 A1 | 7/2008 |
| WO | 2008/091554 A1 | 7/2008 |
| WO | WO 2008/091554 A1 * | 7/2008 |
| WO | 2009/070779 A1 | 6/2009 |
| WO | 01/83800 A2 | 11/2011 |

OTHER PUBLICATIONS

Wilcox, Cleaning up Clostridium difficile infection, vol. 348, pp. 767-768 (1996).
Williams et al., "Effect of Polymeric Adsorbents on the Production of Sanguinarine by Papaver somniferum Cell cultures," Biotechnology and Bioengineering, vol. 40, pp. 971-977 (1992).
International Search Report issued in corresponding International Patent Application No. PCT/EP2014/000091 dated Mar. 19, 2014.
International Preliminary Report on Patentability issued in corresponding International Patent Application No. PCT/EP2014/000091 dated Jul. 21, 2015.
Ackerman et al., "In vitro activity of OPT-80 against Clostridium difficile," Antimicrobial Agents and Chemotherapy, 48 (6): 2280-2282 (2004).
Ansel, H.C., Allen, Jr., L.V., Popovich, N.G., Pharmaceutical Dosage Forms and Drug Delivery Systems, published by Lippincott Williams & Wilkins, pp. 23-26, 179-180, 196 (1999).
Arnone et al., "Structure Elucidation of the Macrocyclic Antibiotic Lipiarmycin," Journal of the Chemical Society, Perkin Transactions 1, Chemical Society, pp. 1353-1359 (1987).
Babakhani et al., "Narrow Spectrum Activity and Low Fecal Protein Binding of Opt-80 and its Major Hydrolysis Metabolite (op-1118)," Program and Abstract of the 47th Interscience Conference on Antimicrobial Agents and Chemotherapy in Chicago, p. 212 (2007).
Bedorf et al., "Isolation and Structure Elucidation of Soraphen A1α, a Novel Antifungal Macrolide from Sorangium cellulosum," Liebigs Ann. Chem., pp. 1017-1021 (1993).
Bolshakov, "Vspomogatelnye veshchestva v technologii lekarstvennykh form," Tekst lektsiy. Leningrad, pp. 27-29 (1991).
Braga et al., "Making crystals from crystals: a green route to crystal engineering and polymorphism," Chem. Commun., pp. 3635-3645 (2005).
Bryn et al., "Solid-State Pharmaceutical Chemistry," Chem. Mater., vol. 6, pp. 1148-1158 (1994).
Bryn et al., "Pharmaceutical Solids: A strategic Approach to Regulatory Considerations," Pharmaceutical Research, 12 (7): 945-954 (1995).
Caira, "Crystalline Polymorphism of Organic Compounds," Topics in Current Chemistry vol. 198: pp. 163-208 (1998).
Caldwell, "Do single enantiomers have something special to offer?," Human Psychopharmacology: Clinical and Experimental, vol. 16, S67-S71 (2001).
Cambridge Crystallographic Data Centre Deposition No. 100349, CCDC No. 114782 (2000).
Cavalleri et al., "Structure and biological activity of lipiarmycin B," The Journal of Antibiotics, 41(3): 308-315 (1988).
Chemical Abstracts registry entry 56645-60-4, Tiacumicin B, Copyright 2007, American Chemical Society, pp. 1-2.
Credito et al., "Activity of OPT-80, a Novel Macrocycle, Compared with Those of Eight Other Agents against Selected Anaerobic Species," Antimicrobial Agent & Chemotherapy, 48(11), pp. 4430-4434.(2004).
Credito et al., "Antianaerobic Activity of OPT 80 Compared to Other Agents," Hershey Medical Center Department of Pathology, (poster), 44th ICAAC (Oct. 30-Nov. 2, 2004) in Chicago.
Davidovich et al., "Detection of Polymorphism by Powder X-Ray Diffraction: Interference by Preferred Orientation," American Pharmaceutical Review, 7(1), pp. 10, 12, 14, 16, 100 (2004).
Dean, Analytical Chemistry Handbook, Published by McGraw-Hill, Inc., pp. 10.23-10.26.
Demain et al., "Manual of Industrial Microbiology and Biotechnology, American Society for Microbiology," pp. 123-126 (1986).
Dykstra et al., "Feedback regulation and the intracellular protein profile of Streptomyces griseus in a cycloheximide fermentaion," Applied Microbiology Biotechnology, vol. 34, pp. 191-197 (1990).
Finegold et al., "In vitro activities of OPT-80 and comparator drugs against intestinal bacteria," Antimicrobial Agents and Chemotherapy, 48(12): 4898-4902 (2004).
Fujii et al., "The Clecarmycins, New Antitumor Antibiotics Produced by Streptomyces: Fermentation, Isolation and Biological Properties," The Journal of Antibiotics, 48(8): 768-772 (1995).
Gastaldo et al., "Improvement of the kirromycin fermentation by resin addition," Journal of Industrial Miclobiology, vol. 16, pp. 305-308 (1996).
Gerber et al., "OPT-80, a macrycyclic antimicrobial agent for the treatment of Clostridium difficile infections: a revew," Expert Opinion on Investivational Drugs, 17(4), pp. 547-553 (2008).
Gerding et al., "Clostridium difficile-associated diarrhea and colitis," Infection Control and Hospital Epidemiology, 16(8): 459-477 (1995).
The Pharmacological Basis of Therapeutics, editors Joel G. Hardman and Lee E. Limbird, consulting editor Alfred Goodman Gilman, published by The McGraw-Hill Companies, Inc., pp. 54-56 (2001).
Guidance for Industry: Container Closure Systems for Packaging Human Drugs and Biologics, U.S. Department of Health and Human Services, Food and Drug Administration (1999).
Hecht, "In Vitro Activities of 15 Antimicrobial Agents against 110 Toxigenic Clostridium difficile Clinical Isolates Collected from 1983 to 2004," Antimicrobial Agents and Chemotherapy, 51(8): 2716-2719 (2007).
Hochlowski et al., "Tiacumicins, A Novel Complex of 18-Membered Macrolides, II Isolation and Structure Determination," The Journal of Antibiotics XL(5), pp. 575-588 (1987).
Hochlowski et al., "Production of Brominated Tiacumicin Derivatives," The Journal of Antibiotics, 50(3): 201-205 (1997).
Jain et al.,"Polymorphism in Pharmacy," Indian Drugs, 23(6), pp. 315-329 (1986).
Jarvis et al., "Use of resins for trichothecene production in liquid cultures," The Journal of Antibiotics, XLIII(11): 1502-1504 (1990).
Lam et al., "Effect of neutral resins on the production of dynemicins by Micromonospora chersina," Journal of Industrial Macrobiology, vol. 5, pp. 453-456 (1995).
Lewiston et al., "Determination of OPT-80 and its Desisobutyryl Metabolite (OP-1118) in Human Plasma by an LC/MS/MS Method," AAPS Journal, American Association of Pharmaceutical Scientists (2005).
Polymorphism in Pharmaceutical Solids, published by Marcel Dekker Inc., edited by Harry G. Brittain pp. 1-2 (1999).

(56) References Cited

OTHER PUBLICATIONS

Pharmaceutical Dosage Forms: Tablets, vol. 2, published by Marcel Dekker, Inc., edited by Lieberman, Lachman, and Schwartz, pp. 462-472.

Marshall et al., "The effect of neutral resins on the fermentation production of rubradirin," Journal of Industrial Microbiology, vol. 5, pp. 283-288 (1990).

Miller et al., "Chromatographic resolution of the enantiomers of a pharmaceutical intermediate from the milligram to the kilogram scale," Journal of Chromatography A, vol. 849, pp. 309-317 (1999).

Morissette et al., "High-throughput crystallization: polymorphs, salts, co-crystals and solvates of pharmaceutical solids," Advanced Drug Delivery Reviews, 56(3): 275-300 (2004).

Okumu et al., "Safety and Pharmacokinetics of OPT-80, a novel antibiotic for treatment of clostridium difficile associated diarrhea (CDAD)," Program and Abstract of the 44th Interscience Conference on Antimicrobial Agents and Chemotherapy, p. 204 (2004).

Poduval et al., "Clostridium difficile and vancomycin-resistant enterococcus: the new nosocomial alliance," The American Journal of Gastroenterology, 95(12): 3513-3515 (2000).

Poxton, "Fidaxomicin: a new macrocyclic, RNA polymerase-inhibiting antibiotic for the treatment of Clostridium difficile Infections," Future Microbiol., 5(4): 539-548 (2010).

Reinke et al., "Update on Clostridium cliff-lode-induced colitis, Part 1," Am. J. Hosp. Pharm., 51(14): 1771-81 (1994).

Remington: The Science and Practice of Pharmacy, 20the Edition, published 2000 by Lippincott Williams and Wilkins, pp. 802-803.

Remington: The Science and Practice of Pharmacy, 20th Edition, editor Daniel Limmer, Published 2000 by the University of the Sciences in Philadelphia, pp. 786, 858, 860 and 1015-1017.

Remington: The Science and Practice of Pharmacy, 21TH Edition, editor David B. Troy, Published 2005 by Lippincott Williams & Wilkins pp. 891 and 1030.

Reville et al., "Tiacumicin B," Drugs of the Future, 31(6): 494-497 (2006).

Shangle et al., "Safety and Pharmacokinetics of OPT-80 in Human Volunteers," Program and Abstract of the 44the Interscience Conference on Antimicrobial Agents and Chemotherapy, Washington DC p. 1 (2004).

Shue et al., "Safety, Tolerance, and Pharmacokinetic Studies of OPT-80 in Healthy Volunteers following Single and Multiple Oral Doses," Antimicrobial Agents and Chemotherapy, 52(4), pp. 1391-1395 (2008).

Sonenshein et al., "Initiation of Transcription in vitro is Inhibited by Lipiarmycin," J. Mol. Biol., vol. 127, pp. 55-72 (1979).

* cited by examiner

Fidaxomicin suspension in water

Immediately after preparation 1h after preparation

Use of HPC-SSL (low viscosity grade)

200mg Fidaxomicin    0.3% HPC-SSL
+0.3w/v% HPC-SSL /5mL

Use of HPC-L (middle viscosity grade)

200mg Fidaxomicin    0.3% HPC-L
+ 0.3w/v% HPC-L /5mL

Use of HPC-SSL (low viscosity grade)

200mg Fidaxomicin    0.3% HPC-SSL
+0.3w/v% HPC-SSL /5mL

200mg Fidaxomicin    0.6% HPC-SSL
+ 0.6w/v% HPC-SSL /5mL

Fig 4

| Lot No. | | OS-4 | OS-5 | OS-6 | OS-7 | OS-8 | OS-9 | OS-12 |
|---|---|---|---|---|---|---|---|---|
| Angle of repose (degree) | | 38 | 36 | 36 | 35 | 37 | 38 | 38 |
| Specific volume | Loose (mL/g) | 2.64 | 2.75 | 2.36 | 2.40 | 2.38 | 2.51 | 2.80 |
| | Tapped (mL/g) | 2.15 | 2.34 | 2.10 | 1.99 | 1.96 | 1.96 | 2.22 |
| Hausner ratio | | 1.23 | 1.18 | 1.12 | 1.21 | 1.21 | 1.28 | 1.26 |

+ Xanthan gum (Keltrol®)

+ Xanthan gum (Keltrol® 630)

+ xanthan gum (Xantural® 180)

+ iota-carrageenan

+ sodium alginate

+ acacia gum

+ guar gum

+ microcrystalline cellulose and sodium carboxymethylcellulose

COMPOSITION OF TIACUMICIN COMPOUNDS

The present invention relates to compositions comprising one or more of a tiacumicin compound as the active ingredient in admixture with an excipient, selected from the group consisting of xanthan gum, carrageenan, sodium alginate, guar gum, water dispersible cellulose (microcrystalline cellulose and sodium carboxymethylcellulose) and mixtures thereof, which is used as an anti-foaming agent.

BACKGROUND OF THE INVENTION

Tiacumicin compounds are naturally occurring compounds with an antibiotic activity that can be obtained by cultivating various microorganisms belonging to the Actinoplanes family (especially the genus *Dactylosporangium aurantiacum*, subspecies *hamdenensis*) in a suitable nutrient medium at a suitable temperature and isolating the compounds having antibiotic activity against a variety of microorganisms (tiacumicins A-F; U.S. Pat. No. 4,918,174). Especially tiacumicins B and C turned out to possess antibiotic activity against a number of Gram-positive bacteria in vitro including strains resistant to therapeutic antibiotics, used at the time. U.S. Pat. No. 5,583,115 discloses dialkyltiacumicin compounds, which are derivatives of the above-mentioned tiacumicin compounds A-F, were found to have in vitro activity against a variety of bacterial pathogens and in particular against *Clostridium* species. U.S. Pat. No. 5,767,096 discloses bromotiacumicin compounds, which are also derivatives of tiacumicin compounds A-F, which were found to have in vitro activity against some bacterial pathogens and in particular against *Clostridium* species.

From a chemical point of view the tiacumicins share an 18-membered macrocyclic ring, which is glycosidically attached to one or two optionally substituted sugar molecules (U.S. Pat. No. 4,918,174 and WO 2004/014295) as follows:

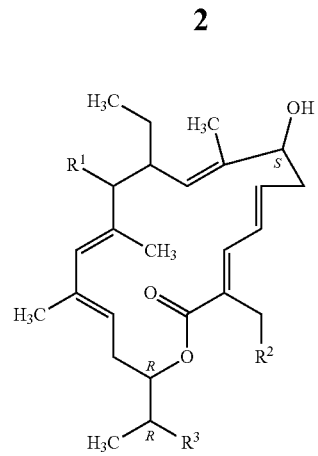

Formula 1

WO 2004/014295 describes substantially pure R-tiacumicins, obtained by submerged aerobic fermentation of *Dactylosporangium aurantiacum hamdenensis*. WO 2006/085838 discloses pharmaceutical compositions containing R-tiacumicins and especially R-tiacumicin B, which contains an R-hydroxyl-group at C19, which shows surprisingly lower MIC values when tested in vitro against *Clostridium* species than the optically pure S-isomer of tiacumicin B and other tiacumicin related compounds.

Chinese patent applications having publication numbers 102030791 and 102219815 respectively and S. Niu et al. (2011) in ChemBioChem 12: page 1740-1748 describe 11 new tiacumicin analogues all lacking the 2'-O-methyl group on the internal rhamnose moiety. Two of those analogues have shown to have improved antibacterial properties.

R-tiacumicin B is also known under the name fidaxomicin (3-[[[6-deoxy-4-O-(3,5-dichloro-2-ethyl-4,6-dihydroxybenzoyl)-2-O-methyl-β-D-mannopyranosyl]oxy]methyl]-12(R)-[[6-deoxy-5-C-methyl-4-O-(2-methyl-1-oxopropyl)-β-D-lyxo-hexopyranosyl]oxy]-11(S)-ethyl-8(S)-hydroxy-18(S)-(1(R)-hydroxyethyl)-9,13,15-trimethyloxacyclooctadeca-3,5,9,13,15-pentaen-2-one or oxacyclooctadeca-3,5,9,13,15-pentaen-2-one, 3-[[[6-deoxy-4-O-(3,5-dichloro-2-ethyl-4,6-dihydroxybenzoyl)-2-O-methyl-β-D-mannopyranosyl]oxy]methyl]-12-[[6-deoxy-5-C-methyl-4-O-(2-methyl-1-oxopropyl)-β-D-lyxo-hexopyranosyl]oxy]-11-ethyl-8-hydroxy-18-[(1R)-1-hydroxyethyl]-9,13,15-trimethyl-, (3E,5E,8S,9E,11S,12R,13E,15E,18S)). It is a compound that has a narrow antimicrobial spectrum, with activity against *Clostridium difficile* and most strains of staphylococci and enterococci but negligible activity against gram-negative organisms and fungi. It is obtained by fermentation of *Dactylosporangium aurantiacum* and corresponds to the following formula (II):

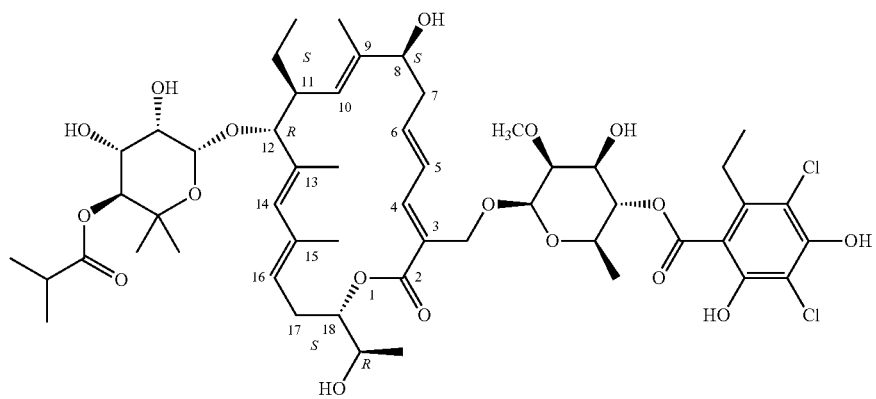

II

According to an in vitro BCS (Biopharmaceutics Classification System) study, fidaxomicin is a BCS Class IV compound (low solubility, low permeability). Upon oral administration fidaxomicin is poorly absorbed from the intestinal tract and is therefore associated with a low incidence of systemic side effects. Fidaxomicin is indicated for the treatment of *Clostridium difficile* infections (CDI) also known as *C. difficile*-associated disease (CDAD) and prevention of recurrences. Along with its narrow antimicrobial spectrum, fidaxomicin also has a prolonged post antibiotic effect against *C. difficile*. Besides the obvious benefit to the patient, the prevention of recurrence would eliminate the costs of treating additional episodes of *C. difficile* infection and should reduce the rate of person-to-person transmission. The recommended dose for adults and elderly people (65 years and older) is 200 mg administered twice daily (q12 h) for 10 days.

Tablets containing 200 mg fidaxomicin are commercially available in Europe (under the trademark Dificlir) and in the USA (under the trademark Dificin). WO 2008/091518 discloses pharmaceutical compositions of tiacumicins, and especially fidaxomicin. In example 1 a tablet formulation is disclosed, which contains 200 mg fidaxomicin in admixture with microcrystalline cellulose, starch, hydroxypropylcellulose, butylated hydroxytoluene, sodium starch glycolate and magnesium stearate. According to example 2 the addition of an anti-oxidant, such as butylhydroxytoluene or butylhydroxyanisole is required in order to prevent the formation of degradation products of fidaxomicin, such as related compound L, which is believed to be an oxidation product of fidaxomicin.

According to the Summary of Product Characteristics the marketed product in Europe is an immediate release tablet, containing microcrystalline cellulose, pregelatinised starch, hydroxypropyl cellulose, butylated hydroxytoluene, sodium starch glycolate and magnesium stearate as the excipients; the tablet is provided with a film-coating, containing polyvinyl alcohol, titanium dioxide, talc, polyethylene glycol and soy lecithin. Adult sick people may experience difficulties when swallowing the tablet.

On the other hand the tablet is not indicated for children. Nowadays Health Authorities require conducting clinical trials in paediatric patient populations with dosage forms that have been specifically developed for these target populations. There are various possibilities for such paediatric dosage forms such as small tablets, dispersible tablets, granulates, powders and granulates for suspension. However, liquid formulations (as such or to be prepared shortly before administration) normally are the formulations of choice for administration to the whole paediatric patient population from birth up till and including childhood. It goes without saying that liquid formulations may also be useful for administration to adult patients, who have difficulties in swallowing tablet formulations.

EP-1652524A1 disclosed in example 1 a dry syrup preparation comprising loratadine as the active ingredient in admixture with hydroxypropylcellulose and a sugar compound. When water was added to form an aqueous suspension, no foaming was observed. The same preparation without hydroxypropylcellulose could not prevent the foaming property.

WO 2005/009474 discloses a dry syrup formulation, comprising a hardly water soluble drug and a specified amount of a hydroxypropyl cellulose with a specified viscosity in water, which formulation after adding water is converted into a uniform dispersion without hardly forming any foam. The formulation may further contain one or more sugars.

US 2006/269485 aimed at seeking a solution for the problem that the addition of an active ingredient to a foam emulsion composition, may destabilise the foam and provides aerosol packages comprising an antibiotic foamable composition, including at least one organic carrier, a surface active agent, at least one polymeric additive such as a gelling agent, water and a gas propellant. Optionally the composition contains a foam adjuvant.

WO 2008/091554 discloses polymorphs of tiacumicin and the preparation thereof. The polymorphs were characterised by X-ray diffraction diagram, melting point and DSC (Differential Scanning calorimetry)-plots, but no further properties were mentioned.

Xanthan gum is an anionic polysaccharide produced by the bacterium *Xanthomonas campestris*. Its structure is composed of a β-(1-4)-D-glucose main chain and side chains each one out of two glucose residues. Side chains are constituted of an α-D-mannose, β-D-glucuronic acid and β-D-mannose as terminal residues. In water, the stiff polymer chain may exist as a single, double or triple helix that interacts with another chain to form a complex, loosely bound network. This particular structure gives the gum its unusual thickening properties, with a yield stress, shear-thinning and thixotropic behaviours. In the pharmaceutical field xanthan gum is used as a suspending, stabilising and thickening agent in oral and topical formulations, for the production of sustained-release matrix tablets or for its muco-adhesive properties (Handbook of pharmaceutical excipients, $6^{th}$ ed.). Several different grades are commercially available (Keltrol, Keltrol 360, Xantural).

Carrageenan according to USP32-NF27 is a hydrocolloid obtained by extraction with water or aqueous alkali from some members of the class Rhodophyceae (red seaweed). It consists mainly of potassium, sodium, calcium, magnesium and ammonium sulfate esters of galactose and 3,6-anhydrogalactose copolymers. These hexoses are alternately linked at the alpha-1,3 and beta-1,4 sites in the polymer. The carrageenans are divided into 3 families according to the position of the sulphate groups and the presence or absence of anhydrogalactose. Lambda-carrageenan is a non gelling polymer containing about 35% ester sulphate by weight and no 3,6-anhydrogalactose. Iota-carrageenan is a gelling polymer containing about 32% ester sulphate by weight and approximately 30% 3,6-anhydrogalactose. Kappa-carrageenan is a strongly gelling polymer containing about 32% ester sulphate by weight and approximately 30% 3,6-anhydrogalactose. The carrageenans have been used in a variety of non parenteral pharmaceutical dosage-forms, including suspensions (wet and reconstitutable), emulsions, gels, creams and lotions as an emulsifying agent, gel base, stabilising agent, suspending agent, sustained-release agent, viscosity increasing agent. In suspension formulations usually the lambda and the iota carrageenan fractions are used.

Guar gum consists of linear chains of (1→4)-beta-D-mannpyranosyl units with alpha-D-galactopyranosyl units attached by (1→6) linkages. The ration of D-galactose to D-mannose is between 1:1.4 and 1:2. It is used as a suspending agent, tablet binder, tablet disintegrant and viscosity increasing agent. Guar gum is a galactomannan, commonly used in cosmetics, food products and pharmaceutical formulations. In oral and topical products guar gum is used as a suspending, thickening and stabilising agent. The USP32-NF27 describes guar gum as a gum obtained from the ground endosperms of *Cyamopsis tetragonulobus*. It consists mainly of a high molecular weight hydrocolloidal polysaccharide, composed of galactan and mannan units combined through glycoside linkages, which may be described chemically as a galactomannan. The main components are polysaccharides composed of D-galactose and D-mannose in molecular ratios of 1:1.4 to 1:2. The molecule consists of a linear chain of beta-(1-4)-glycosidically linked mannopyranoses and single alpha-(1-6)-glycosidically linked galactopyranoses.

Sodium alginate consists mainly of the sodium salt of alginic acid, which is a mixture of polyuronic acids composed of residues of D-mannuronic acid and L-guluronic acid. Sodium alginate is used in a variety of oral and topical pharmaceutical formulations as a stabilising agent, a suspending agent, a disintegrant, a tablet binder and a viscosity increasing agent.

Water dispersible cellulose, also known as "microcrystalline cellulose and carboxymethyl cellulose sodium", e.g. in the U.S. Pharmacopoeia/National Formulary, is used to produce thixotropic gels suitable as suspending vehicles in pharmaceutical and cosmetic formulations. The sodium carboxymethylcellulose aids dispersion and serves as a protective colloid. The water dispersible celluloses are colloidal forms of microcrystalline cellulose, prepared by chemical depolymerisation of highly purified wood pulp, the original crystalline areas of the fibres being combined with sodium carboxymethyl cellulose and spray-dried. These also find wide use as a pharmaceutical and cosmetic excipient, namely as an oil-in-water emulsifier, an emulsion or foam stabilising agent, as a suspending agent in pharmaceutical suspensions (readymade as well as reconstitutable suspension) and as a thickening agent. Four types of the said celluloses have been marketed under trade names as Avicel® RC-501 (containing 7.1-11.9% of sodium carboxylmethyl cellulose), Avicel® RC-581 (containing 8.3-13.8% of sodium carboxymethyl cellulose), Avicel® RC-591 (containing 8.3-13.8% of sodium carboxymethyl cellulose) and Avicel® CL-611 (containing 11.3-18.8% of sodium carboxymethyl cellulose). All types are hygroscopic powders, which are insoluble in organic solvents and dilute acids, and partially soluble in both dilute alkali and water (due to the sodium carboxymethyl cellulose component). Similar products have been marketed under the trade name Ceolus®.

*Acacia* gum or gum arabic is a complex, loose aggregate of sugars and hemicelluloses with a molecular weight of approx. 240,000-580,000. The aggregate consists essentially of an arabic acid nucleus to which are connected calcium, magnesium and potassium along with the sugars arabinose, galactose and rhamnose. *Acacia* is mainly used in oral and topical pharmaceutical formulations as a suspending and emulsifying agent.

In order to enable accurate dosing of fidaxomicin to paediatric patients and to make the product available to the adult patient population with swallowing problems, there is a need for developing an alternative, easy to administer and stable dosage-form comprising fidaxomicin.

SUMMARY OF THE INVENTION

After having carried out detailed investigations, the present inventors have been able to provide a composition comprising as the active ingredient one or more of a tiacumicin compound, a stereo-isomer thereof, a polymorph thereof or a solvate thereof, and an excipient, selected from the group consisting of a xanthan gum, carrageenan, sodium alginate, guar gum, water dispersible cellulose (microcrystalline cellulose and sodium carboxymethylcellulose) and mixtures thereof. This composition, preferably in the form of a granulate, can be administered to the patient as such or can be advantageously and preferably used in the preparation of other suitable dosage-forms, such as an aqueous suspension. Further, the present invention provides the use of a an excipient, selected from the group consisting of a xanthan gum, carrageenan, sodium alginate, guar gum, water dispersible cellulose (microcrystalline cellulose and sodium carboxymethylcellulose) and mixtures thereof as an anti-foaming agent in a composition comprising as the active ingredient one or more of a tiacumicin compound, a stereo-isomer thereof, a polymorph thereof or a solvate thereof.

BRIEF DESCRIPTION OF THE DRAWINGS

FIG. 4 shows an overview of the properties of various granulate formulations containing fidaxomicin and xanthan gum.

DETAILED DESCRIPTION OF THE INVENTION

Figure 1:
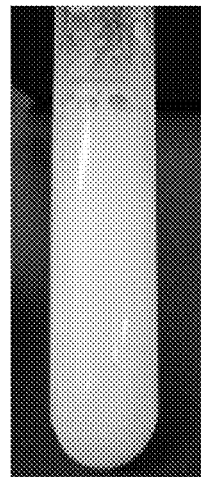
FIG. 1 shows the foaming property of a suspension of fidaxomicin in water, immediately after preparation and 1 hour after preparation.
Figure 1:
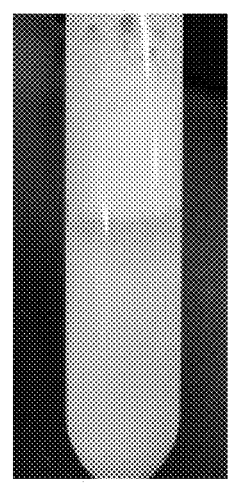

In a first embodiment the present invention relates to an oral pharmaceutical composition comprising as the active ingredient one or more of a tiacumicin compound, a stereo-isomer thereof, a polymorph thereof or a pharmaceutically acceptable solvate thereof, and an excipient, selected from the group consisting of a xanthan gum, carrageenan, sodium alginate, guar gum, water dispersible cellulose (microcrystalline cellulose and sodium carboxymethylcellulose) and mixtures thereof, which is able to prevent the foaming of the tiacumicin compound in water.

The expression "stereo-isomer thereof" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity. The symbols "R" and "S" represent the configuration of substituents around a chiral carbon atom. The isomeric descriptors "R" and "S" are used as described herein for indicating atom configuration relative to a core molecule and are intended to be used as defined in the literature (IUPAC Recommendations 1996, Pure & Applied Chemistry 68: 2193-2222).

The expression "polymorph thereof" describes any alternative crystalline form having different physical properties as a result of the different order of the molecule in a crystal lattice. More specifically, polymorphs such as disclosed in WO2008/091554 are included.

The expression "pharmaceutically acceptable solvate thereof" describes any pharmaceutically acceptable solvate that, administered to a patient (directly or indirectly) provides a tiacumicin compound. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as ethanol is more preferred. A solvent for constituting the solvate is preferably a pharmaceutically acceptable solvent.

The tiacumicin compound according to the present invention has an 18-membered macrocyclic glycoside structure and is a compound as disclosed in U.S. Pat. Nos. 4,918,174; 5,583,115; 5,767,096; and in Chinese patent applications 201010526416.9 and 201110104051.5, herein incorporated by reference. Preferably, the active ingredient is selected from the group consisting of tiacumicin A, tiacumicin B and analogues thereof, (dialkyltiacumicins and bromotiacumicins), tiacumicin C, tiacumicin D, tiacumicin E, tiacumicin F and lipiarmycin. Though all tiacumicin compounds have in common that they are insoluble or almost insoluble in water, more preferably, the active ingredient is lipiarmycin or tiacumicin B or a stereo-isomer thereof or a polymorph thereof. Most preferably R-tiacumicin B (also known as fidaxomicin, OPT-80, or PAR-101) is used as the active ingredient.

The excipient, which acts as an anti-foaming agent, is selected from the group consisting of a xanthan gum, carrageenan, sodium alginate, guar gum, water dispersible cellulose (microcrystalline cellulose and sodium carboxymethylcellulose) and mixtures thereof.

The xanthan gum used can be the naturally occurring polysaccharide as formed by *Xanthomonas campestris* on plants belonging to the cabbage family, but is preferably one that is produced by a fermentation process using the same bacterium and subsequent purification process. A suitable commercially available xanthan gum is Xantural®, a pharmaceutical grade marketed by CP Kelco. However also other commercially available grades, such as Keltrol® and Keltrol® 630, marketed by DSP Gokyo Food & Chemical, can be advantageously be used. Although xanthan gum is known as a viscosity modifying excipient, an emulsion stabilising agent and a foam-stabilising agent, in the compositions according to the present invention it has surprisingly been found to perform not only as a viscosity modifier, thereby keeping the fidaxomicin well suspended in the suspension formed from the granulate compositions according to the present invention after reconstitution with water (which means adding water and vigorously shaking), but also as a good anti-foaming agent for the fidaxomicin, when reconstituted with water. It goes without saying that for the administration of fidaxomicin in a liquid, aqueous formulation to patients, belonging to the adult or paediatric patient population, it is of utmost importance that the dosing of the liquid formulation will occur accurately. This would not have been possible without the addition of xanthan gum, due to the fact that the active ingredient itself has an intrinsic foaming property when put into contact with water.

For each of the following excipients or combinations thereof, the present inventors surprisingly found that these could prevent the foaming of fidaxomicin in water: xanthan gum, carrageenan, particular iota-carrageenan, sodium alginate, guar gum, water dispersible cellulose (microcrystalline cellulose and sodium carboxymethylcellulose).

The present inventors found that when the excipient is selected from the group consisting of hydroxypropylcellulose and *acacia* gum, both excipients often being used in suspension formulations, no such anti-foaming property could be observed and it is difficult to accurately measure a certain amount of the fidaxomicin suspension.

Concentrations of the excipient, acting as an anti-foaming agent, and selected from the group consisting of a xanthan gum, carrageenan, sodium alginate, guar gum, water dispersible cellulose (microcrystalline cellulose and sodium carboxymethylcellulose) and mixtures thereof, to be used in the compositions according to the present invention range from 2.5% w/w-86.5% w/w, the percentage calculated based on the amount of fidaxomicin. However, the preferred concentration ranges depend on the specific excipient, as will be outlined below.

Alternatively the concentrations of the excipient, acting as an anti-foaming agent, and selected from the group consisting of a xanthan gum, carrageenan, sodium alginate, guar gum, water dispersible cellulose (microcrystalline cellulose and sodium carboxymethylcellulose) and mixtures thereof, to be used in the compositions according to the present invention range from 0.12% w/v to 3.5% w/v, the percentage based on an aqueous suspension formulation, obtained by adding water to the dry compositions according to the present invention. A preferred embodiment according to the present invention is a composition in the form of a dry powder, a dry granulate or a dispersible tablet, which after adding water contains 1.0-8.0% w/v, preferably 2.0-6.0% w/v, more preferably 3.0-5.0% w/v, and most preferably about 4.0% w/v of R-tiacumicin B and 0.12-3.5% w/v of an excipient, that is capable of preventing the foaming of fidaxomicin in water. However, the preferred concentration ranges depend on the specific excipient, as will be outlined below.

Concentrations of a xanthan gum to be used in the compositions according to the present invention range from 2.5% w/w to 12.5% w/w, preferably from 5.0 to 6.25% w/w and more preferably 5.0% w/w or 6.25% w/w, the percentage calculated based on the amount of fidaxomicin.

Alternatively the concentrations of a xanthan gum to be used in the compositions according to the present invention range from 0.15% w/v to 0.5% w/v, but are preferably from 0.2% w/v to 0.3% w/v, and are also preferably about 0.3% w/v and more preferably 0.25% w/v, the percentage based on an aqueous suspension formulation, obtained by adding water to the dry compositions according to the present invention. A preferred embodiment according to the present invention is a composition in the form of a dry powder, a dry granulate or a dispersible tablet, which after adding water contains 2.0-6.0% w/v, preferably 3.0-5.0% w/v, and also preferably about 4.0% w/v of R-tiacumicin B and 0.15-0.5% w/v, preferably 0.2-0.3% w/v, and more preferably about 0.25% w/v of a xanthan gum. Another more preferred embodiment according to the present invention is a composition in the form of a dry powder, a dry granulate or a dispersible tablet, which after adding water contains about 4.0% w/v of R-tiacumicin B and 0.2-0.3% w/v of a xanthan gum.

Concentrations of guar gum to be used in the compositions according to the present invention range from 4.8% w/w to 16.25% w/w, the percentage calculated based on the amount of fidaxomicin.

Alternatively the concentrations of guar gum to be used in the compositions according to the present invention range from 0.19% w/v to 0.65% w/v, preferably 0.25-0.55% w/v, and more preferably 0.3-0.4% w/v, the percentage based on an aqueous suspension formulation, obtained by adding water to the dry compositions according to the present invention.

Concentrations of iota-carrageenan to be used in the compositions according to the present invention range from 4.8% w/w to 16.25% w/w, the percentage calculated based on the amount of fidaxomicin.

Alternatively the concentrations of iota-carrageenan to be used in the compositions according to the present invention range from 0.19% w/v to 0.65% w/v, preferably 0.25-0.55% w/v, and more preferably 0.3-0.4% w/v, the percentage based on an aqueous suspension formulation, obtained by adding water to the dry compositions according to the present invention.

Concentrations of sodium alginate to be used in the compositions according to the present invention range from 3.0% w/w to 10.0% w/w, the percentage calculated based on the amount of fidaxomicin.

Alternatively the concentrations of sodium alginate to be used in the compositions according to the present invention range from 0.12% w/v to 0.4% w/v, preferably 0.15-0.3% w/v, and more preferably about 0.2% w/v, the percentage based on an aqueous suspension formulation, obtained by adding water to the dry compositions according to the present invention.

Concentrations of a water dispersible cellulose (microcrystalline cellulose and sodium carboxymethylcellulose) to be used in the compositions according to the present invention range from 10.5% w/w to 86.5% w/w, the percentage calculated based on the amount of fidaxomicin.

Alternatively the concentrations of a water dispersible cellulose (microcrystalline cellulose and sodium carboxymethylcellulose) to be used in the compositions according to the present invention range from 0.42% w/v to 3.5% w/v, preferably 0.8-2.8% w/v, and more preferably 1.2-2.0% w/v, the percentage based on an aqueous suspension formulation, obtained by adding water to the dry compositions according to the present invention.

Alternatively the concentrations of the excipient, acting as an anti-foaming agent, and selected from the group consisting of a xanthan gum, carrageenan, sodium alginate, guar gum, water dispersible cellulose (microcrystalline cellulose and sodium carboxymethylcellulose) and mixtures thereof, preferably a xanthan gum, to be used in the granulate compositions according to the present invention may range from 1.5% w/w to 5.0% w/w, preferably from 1.7% w/w to 4.9% w/w, and more preferably from about 4.0% w/w to about 4.9% w/w, the percentage being calculated on the amount of (dry) granulate. However, the concentration range of the excipient, acting as an anti-foaming agent, and selected from the group consisting of a xanthan gum, carrageenan, sodium alginate, guar gum, water dispersible cellulose (microcrystalline cellulose and sodium carboxymethylcellulose) and mixtures thereof, in the granulate cannot be precisely defined since the granulate according to the invention may contain further excipients.

Preferably it also contains a filler or diluents agent. Examples of such suitable compounds are:

sugars, which may be selected from the group consisting of sucrose, fructose, sorbitol, xylitol, maltitol, aspartame, erythritol, isomalt, trehalose, maltose, mannose, sorbose, xylose, dextran, dextrin, pullulan, mannitol and lactose;

microcrystalline cellulose or microfine cellulose;

starch, a soluble starch or a starch derivative, such as a hydroxyethyl starch;

calcium carbonate, sodium chloride, calcium phosphate, calcium hydrogen phosphate, calcium sulfate, sodium phosphate, carmellose potassium, carmellose calcium, carmellose sodium, synthetic aluminium silicate, etc.

Most preferred are microcrystalline cellulose and a sugar, selected from the group consisting of D-mannitol, erythritol, isomalt and trehalose. However, there is a preference for the use of microcrystalline cellulose, in view of stability of the composition containing fidaxomicin and xanthan gum, under a variety of storage conditions. On top of that for certain groups of patients who should not take sugar-containing compositions, the use of microcrystalline cellulose is advantageous.

The amount of microcrystalline cellulose should be as low as possible, but does not seem to be critical. Alternatively the concentrations of the total of fillers and diluents to be used in the compositions according to the present invention range from 0.0% w/v to 30.0% w/v, the percentages being based on an aqueous suspension formulation, obtained by adding water to the dry compositions according to the present invention.

Alternatively the concentrations of microcrystalline cellulose to be used in the compositions according to the present invention range from 0.0% w/v to 30.0% w/v, but are preferably from 0.0% w/v to 5.0% w/v, more preferably from 0.0% w/v to 2.5% w/v, most preferably from 0.1% w/v to 5.0% w/v and the most preferably 1.0% w/v to 2.0% w/v, the percentages being based on an aqueous suspension formulation, obtained by adding water to the dry compositions according to the present invention.

Alternatively the concentrations of sugar to be used in the compositions according to the present invention range from 0.0% w/v to 30.0% w/v, but are preferably from 0.0% w/v to 25% w/v, more preferably from 0.1% w/v to 25% w/v and most preferably from 1.0% w/v to 20% w/v, the percentages being based on an aqueous suspension formulation, obtained by adding water to the dry compositions according to the present invention.

Alternatively the concentrations of microcrystalline cellulose to be used in the granulate compositions according to the present invention may range from 0.0% w/w to 86.9% w/w, but are preferably from 0.0% w/w to 84.7% w/w, more preferably from 0.0% w/w to 60% w/w, most preferably from 0.0% w/w to 30% w/w and the most preferred from 2.0% w/w to 30% w/w, the percentage being calculated on the amount of (dry) granulate. However, the concentration range of xanthan gum in the granulate cannot be precisely defined since the granulate according to the invention may contain further excipients.

The same is true when a sugar is used.

The granulate may further contain one or more of a disintegrant, since it is important that the fidaxomicin is quickly and uniformly dispersed, both in in vitro and in vivo situations. Suitable disintegrating agents are corn starch, potato starch, partly pregelatinized starch, but also the so-called super-disintegrants can be used; examples of which are crosscarmellose calcium, crosscarmellose sodium, crospovidone, sodium starch glycolate, low-substituted hydroxypropylcellulose and Amberlite IRP 88. A preferred disintegrant is sodium starch glycolate, which is commercially available under the trademark Primojel®. This disintegrant has shown that it is effective in compositions which contain either microcrystalline cellulose or a sugar as the diluents. Further it has shown that it contributes to an easy manufacturing of a granulate composition. Optionally a second disintegrant can be used, such as partly pregelatinised starch. The disintegrant(s) may be present in an amount of up to 10% w/v, preferably 3.0% w/v, most preferably 1.5% w/v and the most preferred 0.3% w/v, the percentages being based on an aqueous suspension formulation, obtained by adding water to the dry compositions according to the present invention.

The composition according to the invention can be used for the preparation of an aqueous suspension, preferably in admixture with excipients, such as buffering agents, preservatives, flavouring agents, sweetening agents and viscosity increasing agents. Most preferably the compositions contain flavouring and sweetening agents to mask the taste of the tiacumicin compounds. The present inventors found that it is difficult to mask the taste of fidaxomicin to an acceptable palatability level, even in the presence of a large amount of a sugar.

Examples of buffering agents are hydrochloric acid, diluted hydrochloric acid, sulfuric acid, adipic acid and its salt, citric acid and its salt, gluconic acid and its salt, succinic acid and its salt, ascorbic acid and its salt, glacial acetic acid and its salt, acetic acid and its salt, tartaric acid and its salt, fumaric acid and its salt, maleic acid and its salt, lactic acid and its salt, malic acid and its salt, phosphoric acid, and its salt, glycine, sodium hydrogencarbonate, sodium carbonate, sodium hydroxide, magnesium hydroxide etc. and combinations of the afore-mentioned agents.

Examples of preservatives are benzoic acid and its salt, an edetate acid and its salt, salicylic acid and its salt, dibutylhydroxytoluene, sorbic acid and its salt, a sodium dehydroacetate, para-hydroxybenzoic acid, and its salt, methylparaben, propylparaben, etc. and combinations of the afore-mentioned preservatives.

Examples of flavouring agents are orange essence, an orange oil, caramel, camphor, cinnamon oil, a spearmint oil, strawberry essence, chocolate essence, a cherry flavour, oil of bitter orange, pineapple oil, mentha oil, a vanilla flavour, bitter essence, a fruits flavour, peppermint essence, a mix flavour, a mint flavour, menthol, lemon powder, a lemon oil, a rose oil etc. and combinations of the afore-mentioned flavouring agents.

Examples of sweetening agents are sucralose, aspartame, fructose, xylitol, glycyrrhizinic acid and its salt, saccharin and its salt, *stevia*, sucrose, sorbitol, glucose, hydrogenated maltose starch syrup, maltitol, maltose, etc. and combinations of the afore-mentioned sweetening agents.

Examples of viscosity enhancing agents are celluloses such as methylcellulose, ethylcellulose, hydroxypropylcellulose, hydroxyethylcellulose, hydroxypropylmethylcellulose, carboxymethylcellulose; gums such as xanthan gum, guar gum, gellan gum, dextran, carrageenan; polyvinylpyrrolidone; specially treated microcrystalline celluloses, such as water dispersible celluloses (microcrystalline cellulose and sodium carboxymethylcellulose); and combinations of the afore-mentioned viscosity enhancing agents.

Alternatively, the granulate according to the invention in admixture with extragranular excipients can be used for the preparation of dispersible tablets for an aqueous suspension.

The composition according to the invention may be an aqueous suspension, a dry powder for an aqueous suspension, a dry granulate for an aqueous suspension or a dispersible tablet for an aqueous suspension.

Other preferable embodiments according to the present invention are as follows:

i) The composition characterized in that it contains 1.0-8.0% w/v of R-tiacumicin B and 0.15-0.5% w/v of an excipient, selected from the group consisting of a xanthan gum, carrageenan, sodium alginate, guar gum, water dispersible cellulose (microcrystalline cellulose and sodium carboxymethylcellulose) and mixtures thereof, which is capable of preventing the foaming of the tiacumicin compound in water, wherein the percentage is based on an aqueous suspension, which is obtained by adding water if the composition is a dry powder, a dry granulate or a dispersible tablet;

ii) the composition according to i), characterized in that the composition contains 4.0% w/v of R-tiacumicin B and 0.2-0.3% w/v of xanthan gum as the excipient;

iii) the composition according to i) or ii), characterized in that it further contains 0.1-5.0% w/v of microcrystalline cellulose and/or 0.1-25% w/v of sugar;

iv) the composition according to i) or ii), characterized in that it further contains 1.0-2.0% w/v of microcrystalline cellulose;

v) the composition according to iii), characterized in that it further contains one or more of a disintegrant in an amount of up to 3.0% w/v, and vi) the composition according to iii), characterized in that it further contains sodium starch glycolate in an amount of up to 0.3% w/v.

It should be noted that for ii) up till and including vi) the percentage is also based on an aqueous suspension, which is obtained by adding water if the composition is a dry powder, a dry granulate or a dispersible tablet.

The dose of the active ingredient in the pharmaceutical composition may readily be determined by the skilled artisan depending on the patient's condition, the disease state, sex, body weight, body surface area, or age. It is to be noted that normally the bacteria and infection state (number of colony forming units per sample) will be determined. In case of an aqueous suspension dosing is based upon volume of reconstituted suspension at 40 mg/mL. 1, 2, 3, 4, or 5 mL is given to the patient based upon the weight of the patients.

A further object of the invention is the use of an excipient, selected from the group consisting of a xanthan gum, carrageenan, guar gum, sodium alginate, water dispersible cellulose (microcrystalline cellulose and sodium carboxymethylcellulose) and mixtures thereof as an anti-foaming agent in a composition comprising one or more of a tiacumicin compound, a stereo-isomer thereof, a polymorph thereof or a solvate thereof.

The following examples further illustrate the invention. It will be apparent to the skilled person that these examples are solely for illustrative purposes and must not be considered to limit the invention.

EXAMPLES

Reference Example 1

To 400 mg of fidaxomicin was added 10 mL of distilled water in a tube. The mixture was shaken and allowed to stand. FIGS. 1/12 shows the result: fidaxomicin has an intrinsically foaming property on contact with water, immediately after preparation as well as 1 hour after preparation.

Reference Example 2

1) Hydroxypropylcellulose

Figure 2:
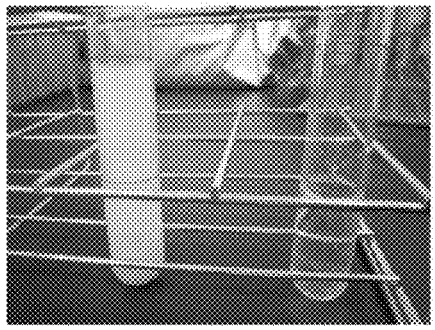
FIG. 2 shows clear solutions of 2 different hydroxypropyl cellulose grades (low and middle viscosity) at 2 different concentrations and the foaming of the same solutions if fidaxomicin is present.
Figure 2:
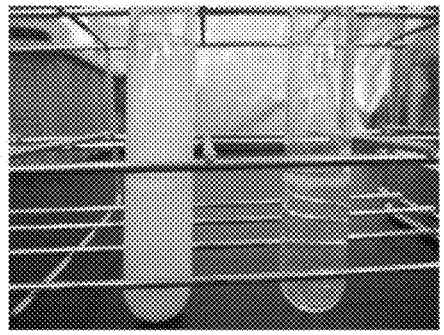
Figure 2:
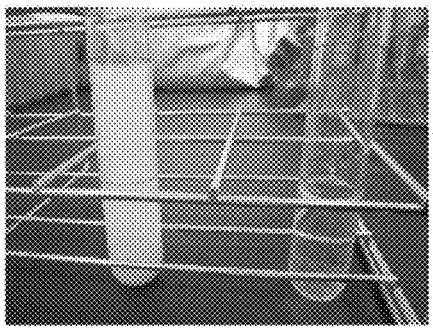
Figure 2:
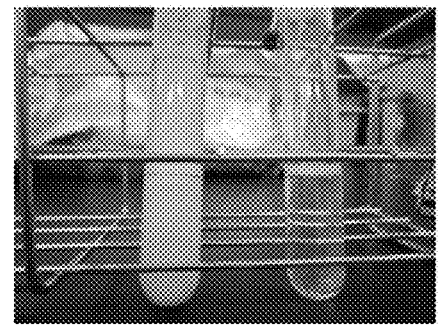

Hydroxypropylcellulose (HPC-L (middle viscosity grade) and HPC-SSL (low viscosity grade) respectively), in a concentration of 0.3 and 0.6 w/v % respectively, was added to 5 mL of distilled water in a tube which contained 0 and 200 mg respectively of fidaxomicin. Each mixture was shaken and allowed to stand. Table 1 and FIGS. 2/12 show the results: hydroxypropylcellulose, in a concentration of 0.3 or 0.6 w/v % in water, does not show any foaming. However when the hydroxypropylcellulose solutions also contained fidaxomicin, the foaming of fidaxomicin could not be prevented.

2) Xanthan Gum

Xanthan gum in a concentration of 0.2% w/v was added to 5 mL of distilled water in a tube, which contained 0 and 200 mg respectively of fidaxomicin. Each mixture was shaken and allowed to stand. Table 1 shows the results: xanthan gum, in a concentration of 0.2% w/v in water, does not show any foaming and is able to prevent the foaming of fidaxomicin.

TABLE 1

| Composition | Foaming property |
|---|---|
| 0.3% HPC-L/5 mL | no |
| 200 mg Fidaxomicin + 0.3 w/v % HPC-L/5 mL | yes |
| 0.3% HPC-SSL/5 mL | no |
| 200 mg Fidaxomicin + 0.3 w/v % HPC-SSL/5 mL | yes |
| 0.6% HPC-SSL/5 mL | no |
| 200 mg Fidaxomicin + 0.6 w/v % HPC-SSL/5 mL | yes |
| 0.2% w/v Xanthan gum (Xantural ®) | no |
| 200 mg Fidaxomicin + 0.2% w/v Xanthan gum (Xantural ®) | no |

Example 1

Fidaxomicin was blended with microcrystalline cellulose Ceolus® PH-101, partially pregelatinised starch (STARCH 1500G), sodium starch glycolate (Primojel®) and xanthan gum (Xantural®) in the amounts as indicated in Table 2a in a vertical granulator (VG-1). Water in an amount as indicated in Table 2a was added to the blend and uniformly distributed to form a wet granulate. Thereafter the granulate was sieved through a 20 mesh sieve, dried at a inlet temperature of 70° C. during 10-20 minutes in a fluid bed dryer, and sieved again but now through a 18 mesh sieve.

TABLE 2a

| Component | Quantity (mg/dosing amount) OS-4 |
|---|---|
| Fidaxomicin | 200.0 |
| Microcrystalline cellulose | 76.0 |
| Partially pregelatinised starch | 40.0 |

TABLE 2a-continued

| Component | Quantity (mg/dosing amount) OS-4 |
|---|---|
| Sodium starch glycolate | 14.0 |
| Xanthan gum | 10.0 |
| Sub-total of granules | 340.0 |
| Process (VG-1) - batch size 163 g | |
| Granulation condition- Impeller speed 400 rpm, chopper speed 3000 rpm | |
| Amount of water | 110 g |
| Total granulation time | 10 min |

The granulate OS-4 was found to have a good quality and good flowability as shown in FIGS. 4/12.

Assessment of Foaming Property of the Suspension Prepared from the Granulate

An amount of the granulate corresponding to 200 mg fidaxomicin was weighed into a tube and 5 ml of water was added. The tube was vigorously shaken for about 1 min. Foaming of the suspension was not observed.

Assessment of Dose Uniformity, Stability for 30 Min after Preparation and Resuspension Capability of the Suspension Prepared from the Granulate.

An amount of the granulate corresponding to 200 mg fidaxomicin was weighed into a tube and 5 mL of water was added. The tube was vigorously shaken for about 1 min. Thereafter samples were taken from the suspension: 3 times from an arbitrary part of the suspension in the tube, one from the upper part, one from the middle part and one from the bottom; 3 times from an arbitrary part of the suspension 30 minutes after preparation and finally 3 times from an arbitrary part of the suspension after resuspending the suspension by vigorously shaking for about 1 minute. The content of fidaxomicin in the samples was assessed by HPLC. The results are shown in Table 2b. A good dose uniformity, a good stability of the suspension for 30 min after preparation and a good resuspension capability were observed.

TABLE 2b

| | Assay of fidaxomicin (%) and RSD |
|---|---|
| Immediately after preparation | Mean: 97.1 |
| (n = 3) | RSD: 2.12 |
| Upper (n = 1) | 99.1 |
| Middle (n = 1) | 98.7 |
| Bottom (n = 1) | 98.1 |
| 30 min after preparation (n = 3) | Mean: 95.7 |
| Re-suspension | Mean: 99.9 |
| (n = 3) | RSD: 1.37 |

In Use Stability Test of Suspension Obtained from the Granulate 300 mg of the granulate of OS-4 was weighed into a bottle, 5 mL of water was added and the bottle was vigorously shaken for about 1 min. Total related substances of fidaxomicin were measured at 0, 5 and 10 days after preparation of the suspension (the results are shown in Table 2c).

TABLE 2c

| Storage condition | OS-4 | | |
|---|---|---|---|
| | day 0 | day 5 | day 10 |
| Room Temperature | Total 2.12% | Total 2.15% | Total 2.10% |
| 5° C. | Total 2.12% | Total 2.13% | Total 2.09% |

Conclusion: the suspension obtained from the granulate OS-4 had a good in-use stability during 10 days after preparation, when stored both at room temperature and at 5° C.

Stability Test of the Granulate

The granulate OS-4 was weighed into bottles which were stored at 70° C. during 9 days (70° C./9D) and 40° C. 75% RH during 1 month (40° C./75% RH/1M), respectively. The amount of related substance was assessed on day 0, day 9 and after 1 month. The results are shown in below Table 2d. Increase of related substances shows the degradation of fidaxomicin. The granulate OS-4 was found to have a good stability.

TABLE 2d

| Lot. No. | OS-4 | | |
|---|---|---|---|
| Storage condition | initial | 70° C./9 D | 40° C./75% RH/1 M |
| Related substances (%) | Total 2.42% | Total 3.47% | Total 2.44% |

Example 2

Fidaxomicin was mixed with varying amounts of xanthan gum (Xantural®) and other additives (i.e. microcrystalline cellulose (Ceolus® PH-101), partially pregelatinised starch (STARCH 1500G), sodium starch glycolate (Primojel®)) in the amounts as indicated in FIGS. 4/13 in a vertical granulator (VG-1). Water in an amount as indicated in Table 3a was added to the blend and uniformly distributed to form a wet granulate. Thereafter the granulate was sieved through a 20 mesh sieve, dried at a inlet temperature of 70° C. during 10-20 minutes in a fluid bed dryer/tray dryer, and sieved again but through a 18 mesh sieve.

TABLE 3a

| | Quantity (mg/dosing amount) | | | | |
|---|---|---|---|---|---|
| Component | OS-5 | OS-6 | OS-7 | OS-8 | OS-9 |
| Fidaxomicin | 200 | 200 | 200 | 200 | 200 |
| Microcrystalline cellulose | 76 | 76 | 76 | 76 | 76 |
| Sodium starch glycolate | 14 | 0 | 7 | 7 | 7 |
| Xanthan gum | 10 | 10 | 10 | 5 | 7.5 |
| Total of granules | 300 | 286 | 293 | 288 | 290.5 |
| Batch size (g) | 144 | 137 | 141 | 138 | 139 |
| Granulation condition - Impeller speed 400 rpm, chopper speed 3000 rpm | | | | | |
| amount of water (g) | 110 | 70 | 80 | 90 | 80 |
| total granulation time (min) | 8 | 6 | 7 | 7 | 7 |
| $D_{50}$ (μm) | 309 | 286 | 113 | 325 | 106 |
| foaming property | no | no | no | no | no |

Results:

The granulates OS-5-OS-9 were found to have good properties such as a good flowability as shown in FIGS. 4/12.

Assessment of Foaming Property of the Suspension Prepared from the Granulates OS-5-OS-9 and of Suspensions OS-10 and OS-11

An amount of each of the granulates OS-5-OS-9, corresponding to 200 mg fidaxomicin, was weighed into a tube and 5 mL of water was added. Further, suspensions OS-10 and OS-11 were prepared by addition of 2.5 mg and 5.0 mg respectively of xanthan gum to a suspension with composition OS-5. Each tube was vigorously shaken for about 1 min. In none of the suspensions foaming was observed.

Assessment of Dose Uniformity and Stability for 30 Min after Preparation of the Suspension Prepared from the Granulates OS-5-OS-9 and of Suspensions OS-10 and OS-11

An amount of each of the granulates OS-5-OS-9, corresponding to 200 mg fidaxomicin, was weighed into a tube and 5 mL of water was added. Further, suspensions OS-10 and OS-11 were prepared by addition of 2.5 mg and 5.0 mg respectively of xanthan gum to a suspension with composition OS-5. Each tube was vigorously shaken for about 1 min. Thereafter samples were taken from the suspension: 3 times from an arbitrary part of the suspension in the tube and 3 times from an arbitrary part of the suspension 30 minutes after preparation. The content of fidaxomicin in the samples was assessed by HPLC. The results are shown in Table 3b and 3c. A good dose uniformity and a good stability for 30 minutes after preparation of the suspensions obtained from the granulates OS-5, OS-6 and OS-7, and of suspension OS-10 and OS-11 were observed.

TABLE 3b

| Assay (%) | OS-5 | OS-6 | OS-7 | OS-8 | OS-9 |
|---|---|---|---|---|---|
| Xanthan gum | 0.2% w/v | 0.2% w/v | 0.2% w/v | 0.1% w/v | 0.15% w/v |
| Immediately after preparation (n = 3) | Mean: 100.6 RSD: 0.42 | Mean: 100.7 RSD: 0.21 | Mean: 101.5 RSD: 0.64 | Mean: 106.3 RSD: 1.07 | Mean: 103.6 RSD: 0.86 |
| 30 min after preparation (n = 3) | Mean: 94.6 RSD: 0.77 | Mean: 93.8 RSD: 1.20 | Mean: 89.5 RSD: 0.95 | Mean: 77.6 RSD: 1.23 | Mean: 86.8 RSD: 0.74 |
| foaming property | no | no | no | no | no |

TABLE 3c

| Assay (%) | OS-10 | OS-11 |
|---|---|---|
| Xanthan gum | 0.25% w/v | 0.3% w/v |
| Immediately after preparation (n = 3) | Mean: 98.3 RSD: 0.70 | Mean: 99.1 RSD: 1.36 |
| 30 min after preparation (n = 3) | Mean: 96.2 RSD: 0.72 | Mean: 98.1 RSD: 1.07 |
| foaming property | no | no |

Example 3

Fidaxomicin was mixed with xanthan gum and other additives in the amount as indicated in Table 4 in a vertical granulator (VG-1). Water in an amount as indicated in Table 4 was added to the blend and uniformly distributed to form a wet granulate. Thereafter the granulate was sieved through a 20 mesh sieve, dried at an inlet temperature of 70° C. during 10-20 minutes in a fluid bed dryer, and sieved again but now through a 18 mesh sieve.

TABLE 4

| Component | Quantity (mg/dosing amount) OS-12 |
|---|---|
| Fidaxomicin | 200 |
| Microcrystalline cellulose | 76 |
| Sodium starch glycolate | 14 |
| Xanthan gum | 12.5 |
| Anhydrous citric acid | 6.05 |
| Sodium citrate dehydrate | 5.45 |
| Total of granules | 314 |
| Batch size (g) | 150 |
| Granulation condition - Impeller speed 400 rpm, chopper speed 3000 rpm | |
| amount of water (g) | 90 |
| total granulation time (min) | 8 |
| $D_{50}$ (µm) | 213 |
| foaming property | no |

Example 4

Fidaxomicin was blended with D-mannitol, sodium starch glycolate (Primojel®) and xanthan gum (Xantural®, a pharmaceutical grade obtained from CP Kelco) in the amounts as indicated in Table 5a in a vertical granulator (VG-1) (the batch size was 160 g). 55 g of water was added to the blend and uniformly distributed to form a wet granulate. The total granulation time was 10 minutes, the impeller was operated at a speed of 400 rpm and the chopper at a speed of 3000 rpm. Thereafter the granulate was sieved through a 20 mesh sieve, dried at a temperature of 70° C. during 10-20 minutes in a fluid bed dryer, and sieved again but now through a 18 mesh sieve.

Granulate composition OS-2 was found to have good flowability and was found to be easily produced thereby providing a high quality granulate. Further, OS-2 had a good dose uniformity.

Stability Testing:

The granulates were transferred into bottles and stored at 5° C. during 10 days and 70° C. during 9 days respectively. Results are shown in Table 5b. Granule OS-2 was found to have a good stability when stored below 70° C.

TABLE 5a

| Component | Quantity (mg/dosing amount) OS-2 |
|---|---|
| Fidaxomicin | 200 |
| D-Mannitol | 755 |
| Sodium starch glycolate | 30 |
| Xanthan gum | 15 |
| Total | 1000 |

TABLE 5b

| | Storage condition | Total related substances (%) |
|---|---|---|
| OS-2 | 5° C./10 days | 1.91 |
| | 70° C./9 days | 4.24 |

Example 5

In the same way as described in example 4, batches were made, containing fidaxomicin, D-mannitol, xanthan gum and optionally sodium starch glycolate (Primojel®). The compositions can be found in Table 6a and the manufacturing conditions, as far as deviating from the procedure as described in example 4, have been summarised in Table 6b.

TABLE 6a

| | Quantity (mg/dosing amount) | |
|---|---|---|
| Component | OS-1 | OS-3 |
| Fidaxomicin | 200 | 200 |
| D-Mannitol | 795 | 762.5 |
| Sodium starch glycolate | — | 30 |
| Xanthan gum | 5 | 7.5 |
| Total | 1000 | 1000 |

TABLE 6b

| Granulation conditions | OS-1 | OS-3 |
|---|---|---|
| Amount of water | 25 g | 55 g |
| Total granulation time | 8 min. | 10 min. |

Assessment of Foaming Property

Figure 3:
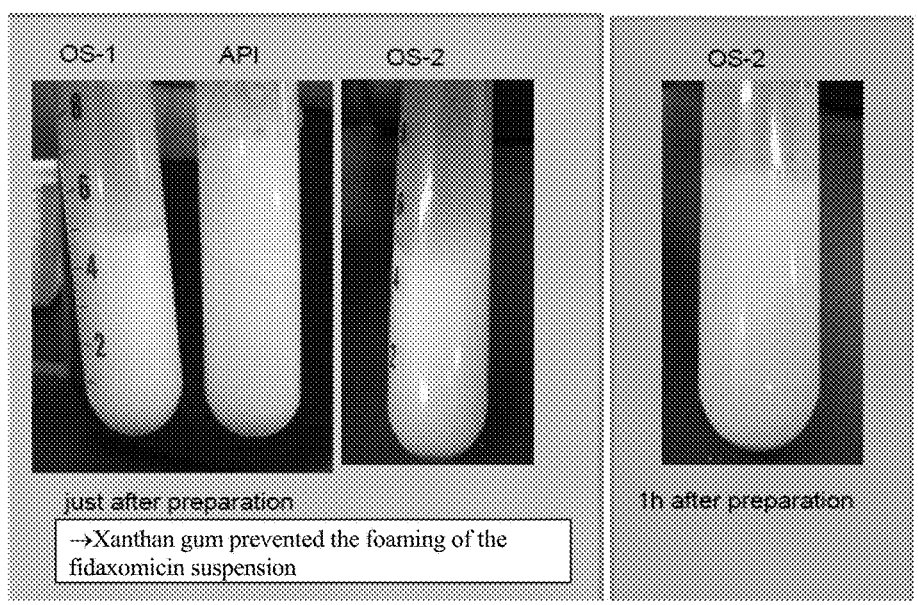
FIG. 3 shows the foaming property of a suspension of fidaxomicin in water (API) as compared to 2 xanthan gum and fidaxomicin containing suspension formulations (OS-1 and OS-2).

Each of the granulate compositions OS-1, OS-2 and OS-3 was weighed into a tube, water was added and the tubes were vigorously shaken for about 1 minute. Foaming property of any of the suspensions OS-1, OS-2 or OS-3 was not observed. See also FIGS. 3/12 for a comparison of the foaming behaviour of some of these suspension formulations with that of fidaxomicin in water.

Example 6

Fidaxomicin and a sugar, selected from the group consisting of D-mannitol, erythritol, isomalt and trehalose, in a ratio of 1:9, were transferred into a glass bottle and stored at 5° C. during 10 days, 70° C. during 9 days and 40° C./75% RH during 1 month, respectively. In the presence of each sugar the degradation of fidaxomicin increased when stored at 70° C. during 9 days. However, when stored at 40° C./75% RH during 1 month the degradation of fidaxomicin did not increase in the presence of the same sugars. This result indicates that these sugars are suitable excipients for a granule formulation for the preparation of fidaxomicin suspension provided the dry granule formulations will be stored at a temperature condition below 70° C. (see Table 7).

TABLE 7

| Composition | Storage condition | Total related substances (%) |
|---|---|---|
| fidaxomicin(control) | 5° C./10 days | 1.91 |
| | 70° C./9 days | 5.10 |
| | 40° C./75% RH/1 M | TBD |
| fidaxomicin:D-mannitol | 5° C./10 days | 2.23 |
| | 70° C./9 days | 5.42 |
| | 40° C./75% RH/1 M | 2.28 |
| fidaxomicin:erythritol | 5° C./10 days | 1.91 |
| | 70° C./9 days | 5.44 |
| | 40° C./75% RH/1 M | 2.24 |
| fidaxomicin:isomalt | 5° C./10 days | 2.25 |
| | 70° C./9 days | 4.03 |
| | 40° C./75% RH/1 M | 2.25 |
| fidaxomicin:trehalose | 5° C./10 days | 2.24 |
| | 70° C./9 days | 4.74 |
| | 40° C./75% RH/1 M | 2.36 |

Example 7

Figure 5:
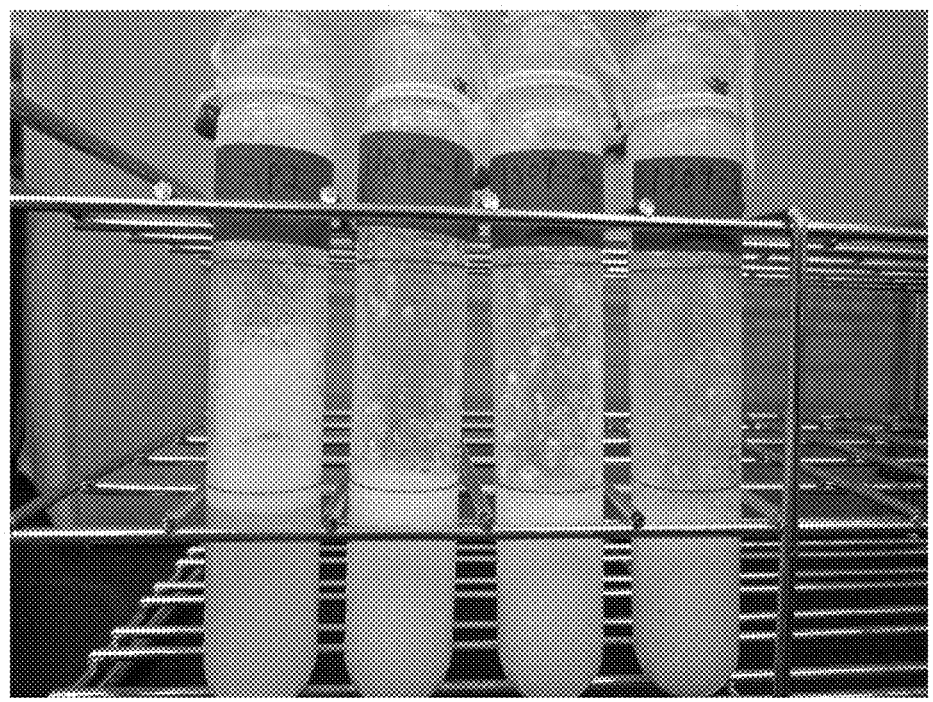
FIG. 5 shows a suspension of fidaxomicin (API) in water and 3 suspensions of fidaxomicin in water to which varying amounts of xanthan gum (Keltrol®) were added.
Figure 6:
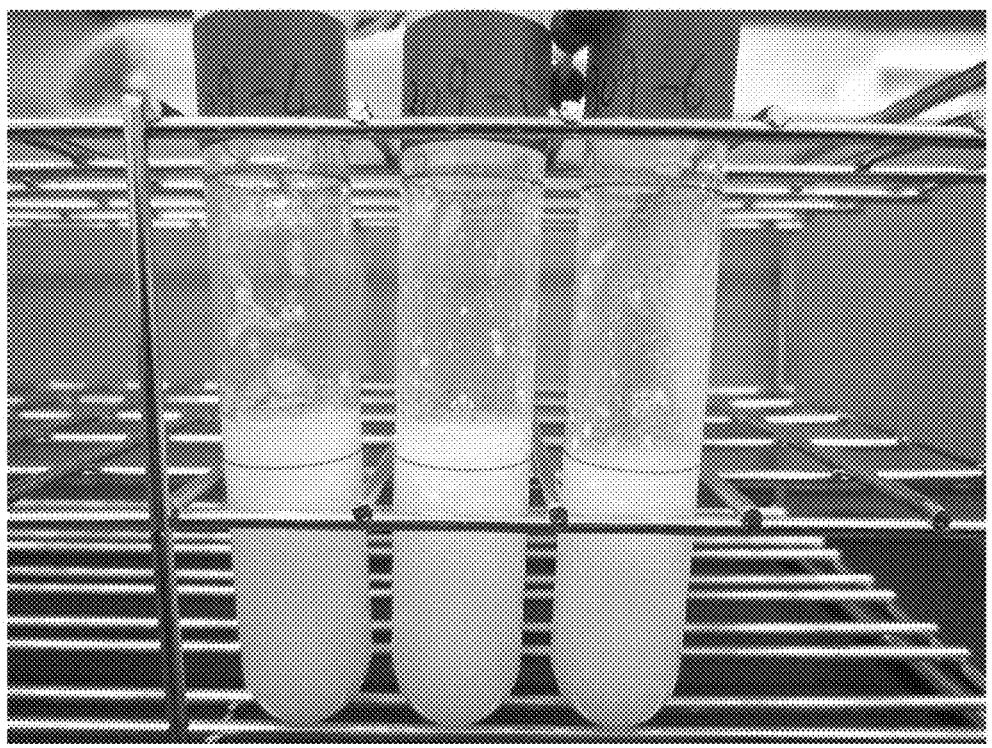
FIG. 6 shows a suspension of fidaxomicin (API) in water and 3 suspensions of fidaxomicin in water to which varying amounts of xanthan gum (Keltrol® 630) were added.

Xanthan gum (Keltrol or the Keltrol 630 grade) in the amount as indicated in Table 8a was added to a glass tube. Subsequently water in the amount as indicated in Table 8a was added to dissolve the xanthan gum. Thereafter fidaxomicin was added to the same glass tube. The glass tube was vigorously shaken for about 1 minute. The foaming property was checked (see Table 8b for the result) and a picture taken (see FIGS. 5/12 and 6/12 respectively).

TABLE 8a

| | Quantity (mg) | | | | | |
|---|---|---|---|---|---|---|
| Component | 1309-1 | 1309-2 | 1309-3 | 1309-4 | 1309-5 | 1309-6 |
| Fidaxomicin (supplier: Biocon) | 200.0 | 200.0 | 200.0 | 200.0 | 200.0 | 200.0 |
| Xanthan gum (Keltrol ®) (Supplier: DSP Gokyo Food & Chemical) | 7.5 | 12.5 | 25.0 | — | — | — |
| Xanthan gum (Keltrol ® 630) (Supplier: DSP Gokyo Food & Chemical) | — | — | — | 7.5 | 12.5 | 25.0 |
| Water | 5 mL | 5 mL | 5 mL | 5 mL | 5 mL | 5 mL |

TABLE 8b

| | Formulation No. | | | | | |
|---|---|---|---|---|---|---|
| | 1309-1 | 1309-2 | 1309-3 | 1309-4 | 1309-5 | 1309-6 |
| Foaming | no | no | no | no | no | no |

Example 8

Figure 7:
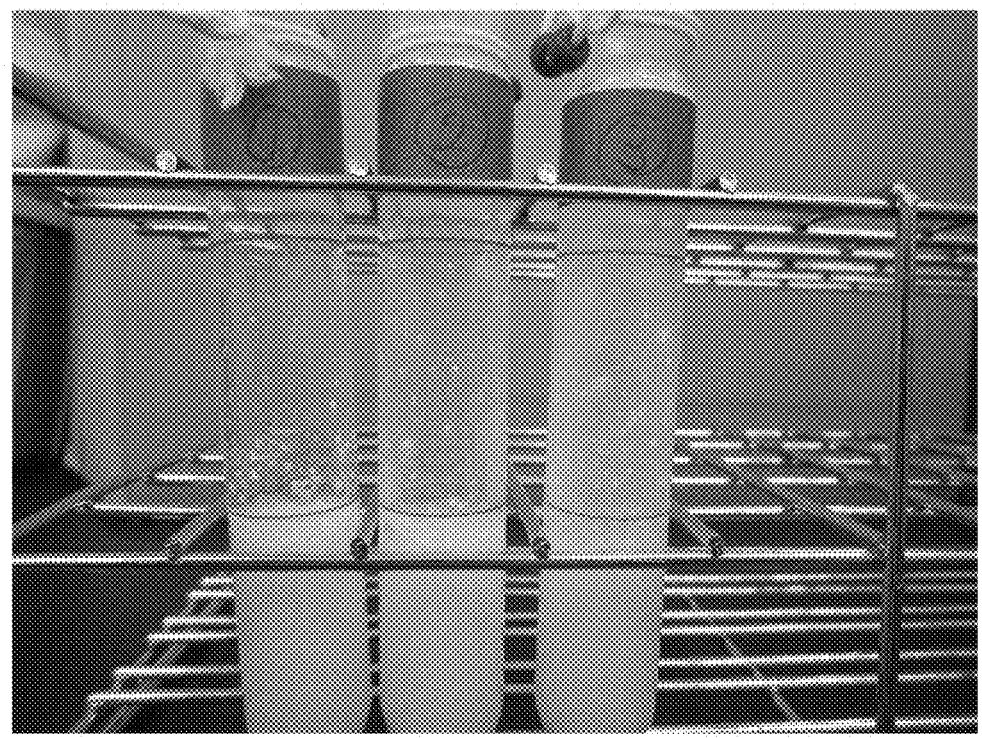
FIG. 7 shows 3 suspensions of fidaxomicin in water to which varying amounts of xanthan gum (Xantural® 180) were added.

Xanthan gum in the amount as indicated in Table 9a was added to a glass tube. Subsequently water in the amount as indicated in Table 9a was added to dissolve the xanthan gum. Thereafter fidaxomicin was added to the same glass tube. The glass tube was vigorously shaken for about 1 minute. The foaming property was checked (see Table 9b for the result) and a picture taken (see FIG. 7/12).

TABLE 9a

| | Quantity (mg) | | |
|---|---|---|---|
| Component | 1 | 2 | 3 |
| Fidaxomicin (Biocon) | 200.0 | 200.0 | 200.0 |
| Xanthan gum (Xantural ® 180) (supplier: Kelco) | 7.5 | 12.5 | 25.0 |
| Water | 5 mL | 5 mL | 5 mL |

TABLE 9b

| | Formulation No. | | |
|---|---|---|---|
| | 1 | 2 | 3 |
| Foaming | no | no | no |

Example 9

Figure 8:
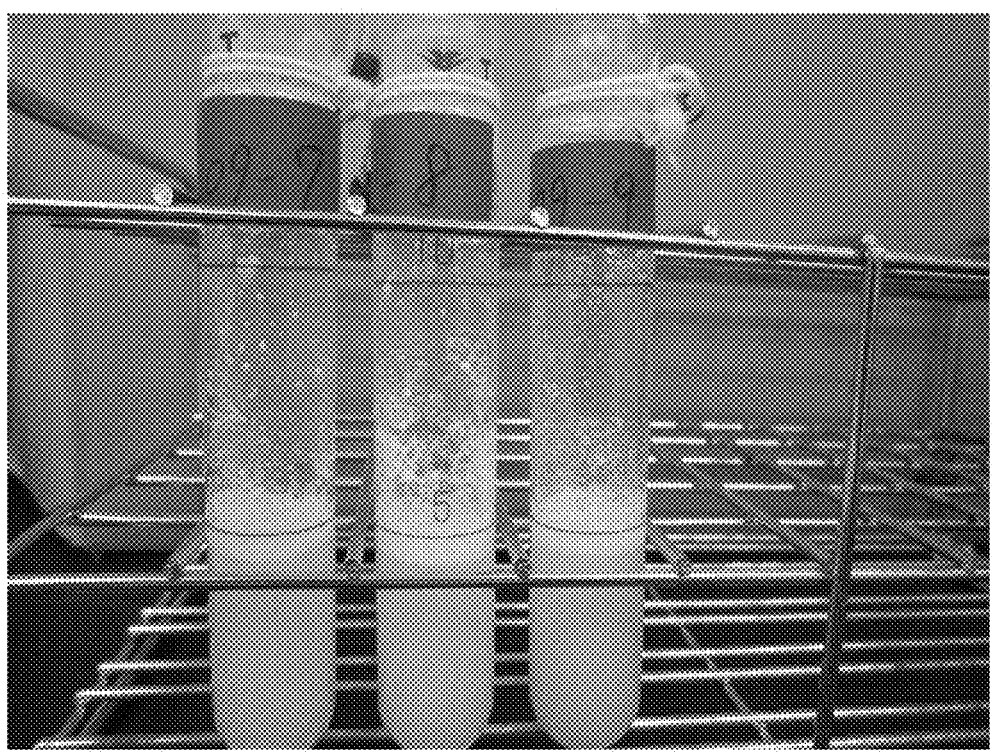
FIG. 8 shows 3 suspensions of fidaxomicin in water to which varying amounts of iota-carrageenan (Soageena®) were added.
Figure 9:
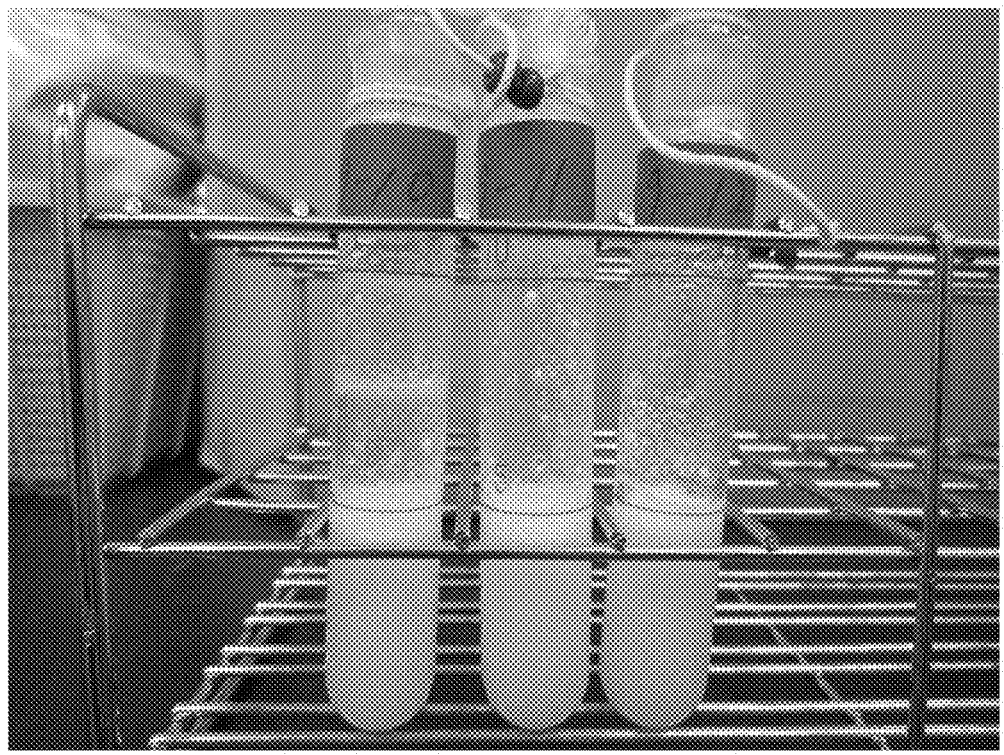
FIG. 9 shows 3 suspensions of fidaxomicin in water to which varying amounts of sodium alginate (Duck Algin®) were added.

Iota-carrageenan (Soageena®, MRC-Polysaccharide) or sodium alginate (Duck Algin®; Kikkoman) in the amount as indicated in Table 10a was added to a glass tube. Subsequently water in the amount as indicated in Table 10a was added to dissolve iota-carrageenan or sodium alginate. Thereafter fidaxomicin was added to the same glass tube. The glass tube was vigorously shaken for about 1 minute. The foaming property was checked (see Table 10b for the result) and a picture taken (see FIGS. 8/12 and 9/12 respectively).

TABLE 10a

| | Quantity (mg) | | | | | |
|---|---|---|---|---|---|---|
| Component | 1309-7 | 1309-8 | 1309-9 | 1309-10 | 1309-11 | 1309-12 |
| Fidaxomicin (Biocon) | 200.0 | 200.0 | 200.0 | 200. | 200.0 | 200.0 |
| ι-carrageenan | 9.75 | 16.25 | 32.5 | — | — | — |
| Sodium alginate | — | — | — | 6.0 | 10.0 | 20.0 |
| Water | 5 mL | 5 mL | 5 mL | 5 mL | 5 mL | 5 mL |

TABLE 10b

| | Formulation No. | | | | | |
|---|---|---|---|---|---|---|
| | 1309-7 | 13098 | 1309-9 | 1309-10 | 1309-11 | 1309-12 |
| Foaming | no | no | no | no | no | no |

Example 10

Figure 10:
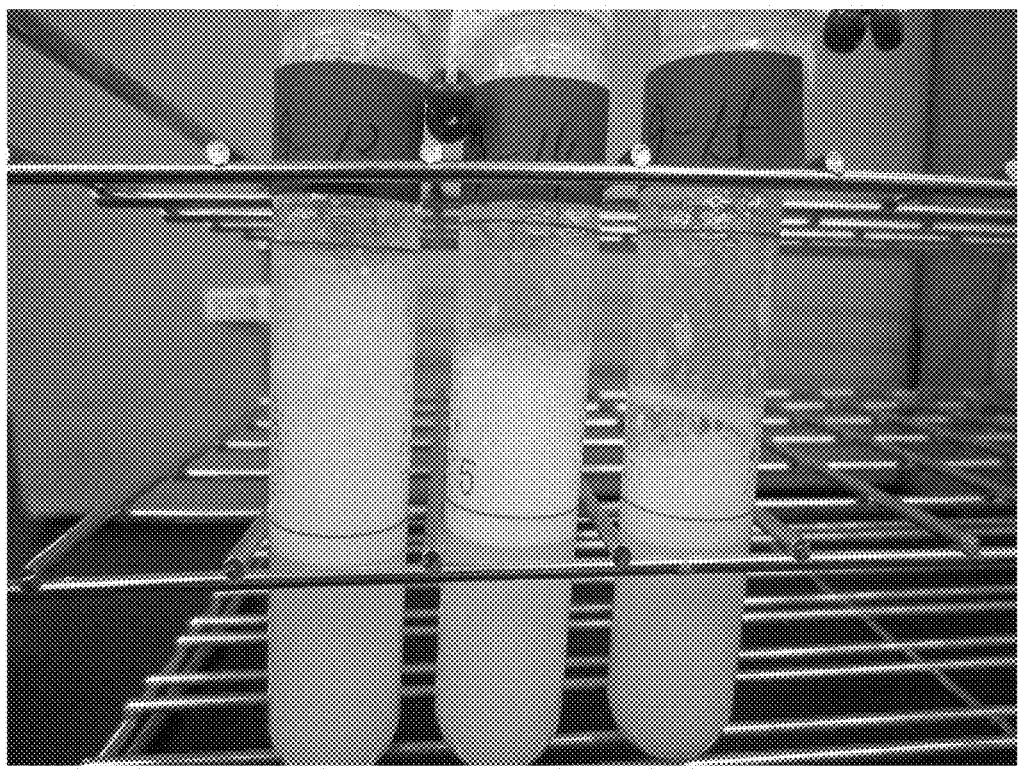
FIG. 10 shows 3 suspensions of fidaxomicin in water to which varying amounts of *acacia* gum (Gum Arabic®) were added.
Figure 11:
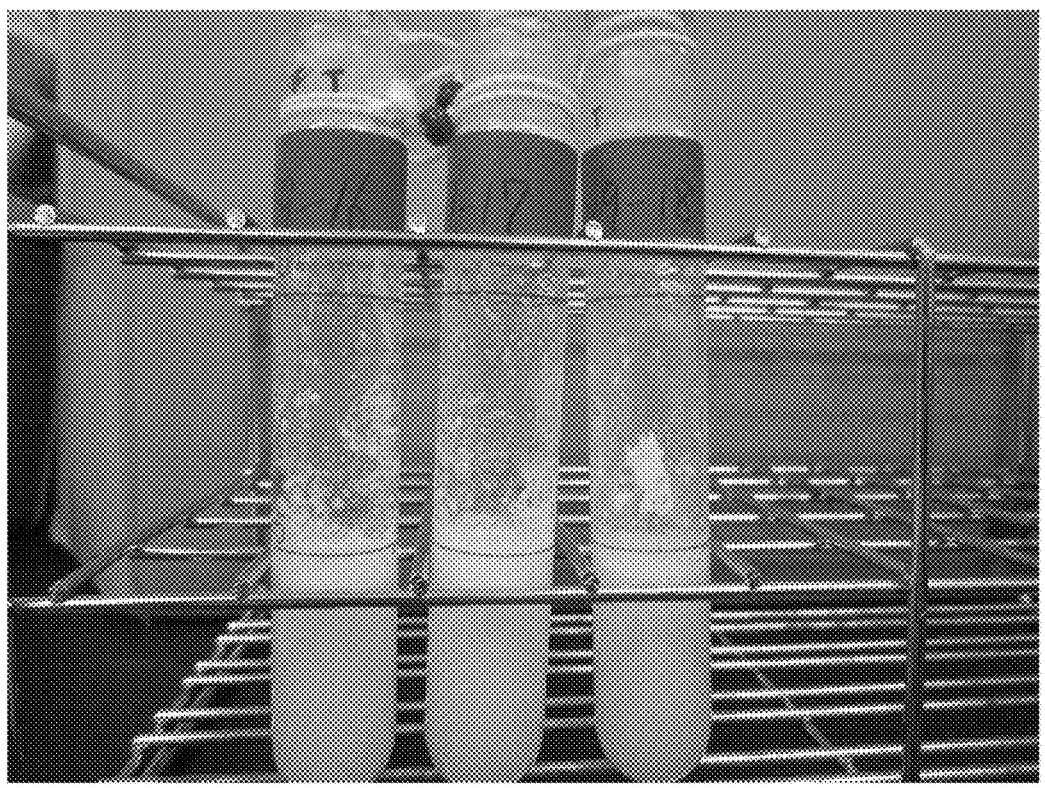
FIG. 11 shows 3 suspensions of fidaxomicin in water to which varying amounts of guar gum (Vistop®) were added.

*Acacia* gum (Gum Arabic®, DSP Gokyo&Chemical) or guar gum (Vistop®; San-Ei Gen F.F.I.) in the amount as indicated in Table 11a was added to a glass tube. Subsequently water in the amount as indicated in Table 11a was added to dissolve the *acacia* or the guar gum. Thereafter fidaxomicin was added to the same glass tube. The glass tube was vigorously shaken for about 1 minute. The foaming property was checked (see Table 11b for the result) and a picture taken (see FIGS. 10/12 and 11/12 respectively).

TABLE 11a

| | Quantity (mg) | | | | | |
|---|---|---|---|---|---|---|
| Component | 1309-13 | 1309-14 | 1309-15 | 1309-16 | 1309-17 | 1309-18 |
| Fidaxomicin | 200.0 | 200.0 | 200.0 | 200.0 | 200.0 | 200.0 |
| Acacia gum | 25.0 | 50.0 | 250.0 | — | — | — |
| Guar gum | — | — | — | 9.75 | 16.25 | 32.5 |
| Water | 5 mL | 5 mL | 5 mL | 5 mL | 5 mL | 5 mL |

TABLE 11b

| | Formulation No. | | | | | |
|---|---|---|---|---|---|---|
| | 1309-13 | 1309-14 | 1309-15 | 1309-16 | 1309-17 | 1309-18 |
| Foaming | yes | yes | yes | no | no | no |

Example 11

Microcrystalline cellulose and sodium carboxymethylcellulose (water dispersible cellulose; Ceolus RC-A591NF)

Figure 12:
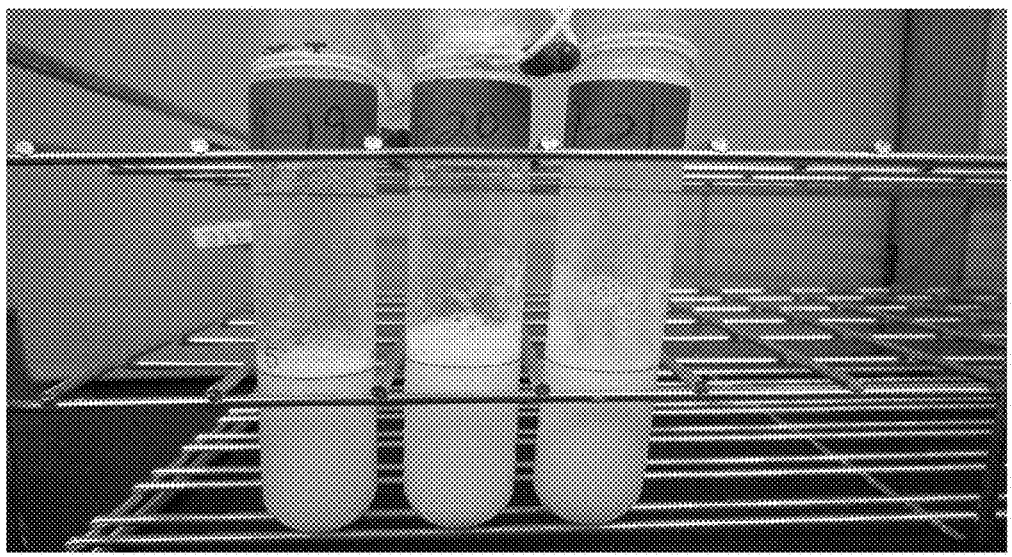
FIG. 12 shows 3 suspensions of fidaxomicin in water to which varying amounts of water dispersible cellulose (microcrystalline cellulose and sodium carboxymethylcellulose) (Ceolus® RC-A591NF) were added.

(from Asahikasei Chemicals) in the amount as indicated in Table 12a was added to a glass tube. Subsequently water in the amount as indicated in Table 12a was added to disperse the microcrystalline cellulose and sodium carboxymethylcellulose. Thereafter fidaxomicin was added to the same glass tube. The glass tube was vigorously shaken for about 1 minute. The foaming property was checked (see Table 12b for the result) and a picture taken (see FIGS. 12/12).

TABLE 12a

| | Quantity (mg) | | |
|---|---|---|---|
| Component | 1309-19 | 1309-20 | 1309-21 |
| Fidaxomicin | 200.0 | 200.0 | 200.0 |
| Ceolus RC-A591NF | 21.0 | 86.5 | 173.0 |
| Water | 5 mL | 5 mL | 5 mL |

TABLE 12b

| | Formulation No. | | |
|---|---|---|---|
| | 1309-19 | 1309-20 | 1309-21 |
| Foaming | no | no | no |

Example 12

Fidaxomicin was blended with microcrystalline cellulose (Ceolus® PH-101), sodium starch glycolate (Primojel®) and xanthan gum (Xantural®) in the amounts as indicated in Table 13 in a vertical granulator (VG-1). Water in an amount as indicated in Table 13 was added to the blend and uniformly distributed to form a wet granulate. Thereafter the granulate was sieved through a 20 mesh sieve, dried at a inlet temperature of 70° C. during 10-20 minutes in a fluid bed dryer, and sieved again but now through a 18 mesh sieve.

The foaming property of the suspension prepared from the granulate and the dispersibility were assessed as in example 1.

TABLE 13

| | Quantity (mg/dosing amount) | | | |
|---|---|---|---|---|
| Component | 1310G01 | 1310G02 | 1310G03 | 1310G04 |
| Fidaxomicin | 200.0 | 200.0 | 200.0 | 200.0 |
| Microcrystalline Cellulose | 5.0 | 1250.0 | 1500.0 | 0.0 |
| Sodium starch glycolate | 14.0 | 14.0 | 14.0 | 14.0 |
| Xanthan gum | 12.5 | 12.5 | 12.5 | 12.5 |
| Total | 231.5 | 1476.5 | 1726.5 | 226.5 |
| Amount of water used for granulation (g) | 125 | 1200 | 1100 | 125 |
| Manufacturability | yes | yes | yes | yes |
| foaming | no | no | no | no |
| Dispersibility | yes | yes | Δ* | yes |

Note:
*not so good because of high viscosity

INDUSTRIAL APPLICABILITY

The granule compositions according to the present invention show many advantages. They can be administered as such, but preferably they can be easily used to prepare an aqueous suspension containing the required dose for the patient, either an adult or a paediatric one. The suspension so obtained can be administered immediately after reconstitution; however the stability may allow for administration of the suspension up to 30 minutes after reconstitution. The viscosity of the suspension allows administration by oral syringe, dosing cup or even gastric tubing. The so obtained suspensions can be easily administered in a small volume and this means that the patient compliance will be increased. Further due to the good stability of the dry dosage forms they can be easily stored at room temperature and without the need of any special storage conditions.

Although sugar-containing compositions form part of the invention, the present invention also provides for sugar-free compositions. On top of that the compositions according to the invention do not contain surfactants.

The use of an excipient, selected from the group consisting of a xanthan gum, carrageenan, sodium alginate, guar gum, water dispersible cellulose (microcrystalline cellulose and sodium carboxymethylcellulose) and mixtures thereof as an anti-foaming agent for fidaxomicin, when put in contact with water, has resulted in suspension formulations that can be accurately dosed to the patients.

The invention claimed is:

1. A pharmaceutical composition comprising as the active ingredient a tiacumicin B compound, analogues thereof, a stereo-isomer thereof, a polymorph thereof or a pharmaceutically acceptable solvate thereof, and xanthan gum as an excipient, wherein the excipient is present in an amount to prevent foaming of the tiacumicin B compound in water.

2. The composition according to claim 1, wherein the active ingredient is fidaxomicin.

3. The composition according to claim 1, wherein the composition further contains microcrystalline cellulose or a sugar.

4. The composition according to claim 3, wherein the sugar is selected from the group consisting of D-mannitol, erythritol, isomalt and trehalose.

5. The composition according to claim 1, wherein the composition further contains one or more of a disintegrant.

6. The composition according to claim 1, wherein the composition further contains sodium starch glycolate.

7. The composition according to claim 1, wherein the composition further contains partially pregelatinised starch.

8. The composition according to claim 1, wherein the composition is in the form of a dry powder for an aqueous suspension, a dry granulate for an aqueous suspension or a dispersible tablet for an aqueous suspension.

9. The composition of claim 1, wherein the analogue of tiacumicin B is selected from the group consisting of dialkyltiacumicins and bromotiacumicins.

10. The composition of claim 1, wherein the pharmaceutical composition is an oral pharmaceutical composition.

* * * * *